(12) United States Patent
Matsuno et al.

(10) Patent No.: US 8,826,725 B2
(45) Date of Patent: Sep. 9, 2014

(54) GAS DETECTOR

(75) Inventors: Toshihiro Matsuno, Komaki (JP);
Masaya Watanabe, Komaki (JP); Shoji Kitanoya, Kasugai (JP)

(73) Assignee: NGK Spark Plug Co., Ltd., Aichi (JP)

( * ) Notice: Subject to any disclaimer, the term of this patent is extended or adjusted under 35 U.S.C. 154(b) by 726 days.

(21) Appl. No.: 13/025,192

(22) Filed: Feb. 11, 2011

(65) Prior Publication Data
US 2012/0204623 A1    Aug. 16, 2012

(51) Int. Cl.
G01N 25/30    (2006.01)
G01N 25/20    (2006.01)
G01N 25/18    (2006.01)

(52) U.S. Cl.
CPC ..................... *G01N 25/18* (2013.01)
USPC ........................ 73/25.03; 73/25.05

(58) Field of Classification Search
USPC .................... 73/23.31, 25.03, 25.05
See application file for complete search history.

(56) References Cited

U.S. PATENT DOCUMENTS

| | | | |
|---|---|---|---|
| 6,513,364 B1* | 2/2003 | Jonda et al. | 73/31.06 |
| 2002/0142478 A1 | 10/2002 | Wado et al. | 436/151 |
| 2002/0187075 A1* | 12/2002 | Nadanami et al. | 422/98 |
| 2004/0182705 A1* | 9/2004 | Ishikawa et al. | 204/424 |
| 2006/0049048 A1* | 3/2006 | Kondo et al. | 204/425 |
| 2006/0110609 A1* | 5/2006 | Eaton et al. | 428/446 |
| 2006/0194332 A1 | 8/2006 | Wado et al. | 436/151 |
| 2008/0282771 A1* | 11/2008 | Hamatani et al. | 73/23.31 |

FOREIGN PATENT DOCUMENTS

| | | | |
|---|---|---|---|
| JP | 2002-286673 | 10/2002 | G01N 27/12 |
| JP | 2005-156364 | 6/2005 | G01N 27/16 |
| JP | 2005-164570 | 6/2005 | G01N 27/12 |
| JP | 2007-327806 | 12/2007 | G01N 27/16 |

OTHER PUBLICATIONS

Machine Translation of JP 2005-156364, Detailed Description. Translation obtained on Aug. 26, 2013 from <http://www19.ipdl.inpit.go.jp/PA1 /cgi-bin/PA1INDEX>.*
Machine Translation of JP 2005-164570. Detailed Description. Translation obtained on Aug. 26, 2013 from <http://www19.ipdl.inpit.go.jp/PA1/cgi-bin/PA1INDEX>.*
Salama, C. A. T. "RF sputtered aluminum oxide films on silicon," J. Electrochem.1 Soc.: Solid State Science. Jul. 1970. pp. 913-917.*
A. Khanna and D. G. Bhat, "Nanocrystalline gamma alumina coatings by inverted cylindrical magnetron sputtering," Surface & Coatings Technology 201 (2006) 168-173.*
Notification of Reasons for Refusal (dated Jun. 12, 2012) issued in connection with corresponding Japanese Patent Application No. 2008-270164, with English translation.

* cited by examiner

*Primary Examiner* — Lisa Caputo
*Assistant Examiner* — Punam Roy
(74) *Attorney, Agent, or Firm* — Kusner & Jaffe (57) ABSTRACT

A gas detector for use in, for example, measuring the concentration of flammable gas or detecting leakage of flammable gas. The gas detector has a gas detection element in which at least a heat-generating resistor and an insulation layer are laminated on a semiconductor substrate made of silicon while the insulation layer encloses the heat-generating resistor. The gas detector detects flammable gas on the basis of temperature and resistance of the heat-generating resistor which vary according to flammable gas. In the gas detection element, a protection layer in the form of a gas impermeable oxide film is provided on its outermost surface which comes into contact with an environmental atmosphere that contains flammable gas. Thus, alkali resistance is ensured. Since the protection layer is impermeable to gas, entry of impurities (organic silicon) contained in the environmental atmosphere into the protection layer is restrained, whereby output is stabilized and becomes accurate.

10 Claims, 8 Drawing Sheets

FIG. 5A
FIRST STEP

FIG. 5D
FOURTH STEP

FIG. 5B
SECOND STEP

FIG. 5E
FIFTH STEP

FIG. 5C
THIRD STEP

FIG. 5F
SIXTH STEP

<Test results>   Gas conditions: HMDS = 400 ppm; $H_2$ = 1000 ppm; Air bal.
   80°C; Dry; 3 L/min (0.02 m/s)
Test time: 250 h
Heater temperature: 400°C <Test apparatus>

<Test results>

| Type of protection layer | Change in voltage (mV) |
|---|---|
| No protection layer | 0 |
| Alumina sol | 16.0 |
| Alumina sputtered | −0.6 |

FIG. 11

<Test conditions>

(1) Immerse the gas detection elements in a 1 mol NaOH solution for 5 seconds.
(2) Dry the gas detection elements at room temperature.
(3) Leave the gas detection elements for 24 hours within the pressure test apparatus whose inner temperature is held at 120°C (unenergized).
(4) Count damaged gas detection elements.

<Test apparatus>

FIG. 12

<Test results>

| Type of protection layer | Number of damaged elements |
|---|---|
| No protection layer | 12/18 |
| Alumina sol | 0/18 |
| Alumina sputtered | 0/18 |

GAS DETECTOR

FIELD OF THE INVENTION

The present invention relates to a gas detector for use in, for example, measuring the concentration of flammable gas or detecting leakage of flammable gas.

BACKGROUND OF THE INVENTION

In view of implementation of space saving and low power consumption, demand exists to further reduce the size of gas detectors for measuring the concentration of flammable gas or detecting leakage of flammable gas. In recent years, gas detection elements with greatly reduced sizes have been developed by use of MEMS (Micro-Electro-Mechanical System) technology (also called the micromachining technique). A gas detection element formed by use of MEMS technology is configured such that a plurality of thin films are formed in layers on a semiconductor substrate (e.g., a silicon substrate).

Examples of such a gas detection element include a thermal-conductivity-type gas detection element and a catalytic-combustion-type gas detection element. The thermal-conductivity-type gas detection element has a heat-generating resistor and utilizes the phenomenon that, when the heat-generating resistor is energized and generates heat, heat is conducted to flammable gas. Specifically, in the case of controlling the gas detection element at a constant temperature, conduction of heat causes a change in temperature of the heat-generating resistor and thus a change in resistance of the heat-generating resistor. On the basis of the amount of the change, "gas-to-be-detected" is detected. The catalytic-combustion-type gas detection element has a heat-generating resistor and a catalyst, which causes combustion of flammable gas by means of heat of the heat-generating resistor. The catalytic-combustion-type gas detection element utilizes the phenomenon that, when the heat-generating resistor is energized, the catalyst causes combustion of flammable gas. Specifically, the heat-generating resistor changes in temperature and resistance according to heat of combustion of flammable gas. On the basis of the amount of the change, flammable gas is detected.

In both the thermal-conductivity-type gas detection element and the catalytic-combustion-type gas detection element, the resistance of the heat-generating resistor varies with the type or concentration of flammable gas. Thus, a gas detector having such a gas detection element can detect flammable gas on the basis of the resistance of the heat-generating resistor.

Such a gas detection element is configured as follows: an insulation layer is disposed on a semiconductor substrate, and a heat-generating resistor is disposed in the insulation layer. Preferably, the outermost surface (specifically, a surface which comes into contact with a gaseous atmosphere that contains flammable gas) of the insulation layer has excellent corrosion resistance and excellent stability. A gas detection element fabricated by use of MEMS technology may be configured such that the outermost surface of the insulation layer is of silicon nitride. See Japanese Patent Application Laid-Open (kokai) No. 2005-156364 (hereinafter "Patent Document 1"). However, silicon nitride or a like material may tend to be corroded by an alkali substance adhering thereto. Thus, improvement in durability against alkali substance is desired.

In order to prevent corrosion caused by adhesion of an alkali substance, provision of a protection layer resistant to alkali (hereinafter, referred to as the alkali-resistant protection layer) on the surface formed of silicon nitride or the like is conceived. For example, see Japanese Patent Application Laid-Open (kokai) No. 2005-164570 (hereinafter "Patent Document 2"). According to Patent Document 2, the alkali-resistant protection layer is formed by a so-called spin coating process. Specifically, alumina sol is applied to the surface in a layered manner, followed by firing. By this process, an alumina layer (i.e., an alkali-resistant protection layer) is formed. Notably, both Patent Documents 1 and 2 were filed by the applicant of the present application.

Problems to be Solved by the Invention

Needless to say, a gas detector whose gas detection element is improved in performance (durability such as alkali resistance) as in the case of Patent Document 2 is an excellent one. However, in recent years, demand has arisen to provide higher detection accuracy in addition to such improvement in performance.

The applicant of the present application carried out extensive studies, and as a result, found that, for example, the gas detector described in Patent Document 2 leaves room for improvement of detection accuracy.

First, an environmental atmosphere which contains flammable gas may contain impurities (e.g., organic silicon) to a certain extent, and such impurities may have an effect on output of the gas detection element. Specifically, according to Patent Document 2, an alkali-resistant protection layer is formed through firing. In this case, the alkali-resistant protection layer has a porous structure. Accordingly, it cannot be denied that impurities are caught in pores of the alkali-resistant protection layer, and an associated change in thermal capacity of the gas detection element arises (i.e., output of the gas detection element is susceptible to error).

SUMMARY OF THE INVENTION

The present invention has been conceived in view of the above circumstances, and an object of the present invention is to attain high durability and high detection accuracy for a gas detector for use in, for example, measuring the concentration of flammable gas or detecting leakage of flammable gas.

Means for Solving the Problems

To achieve the above object, a first embodiment of the present invention provides a gas detector comprising a gas detection element and control means. The gas detection element is configured such that at least a heat-generating resistor and an insulation layer are laminated on a semiconductor substrate, and the insulation layer covers the heat-generating resistor. The control means controls energization of the heat-generating resistor and detects gas-to-be-detected on the basis of resistance of the energized heat-generating resistor. In the gas detector, the gas detection element has a gas impermeable oxide film laminated on a surface of the insulation layer in such a manner as to cover the insulation layer, and the gas impermeable oxide film forms an outermost surface layer which comes into contact with a gaseous atmosphere that contains the gas-to-be-detected.

The term "detect" in the present invention means not only to judge whether or not gas-to-be-detected exists, but also to measure the concentration of gas-to-be-detected. The expression that the oxide film is impermeable to gas means that the oxide film is formed densely to such an extent as not to allow gas to pass therethrough.

In the gas detector according to the first embodiment, the outermost surface layer of the gas detection element is formed of the oxide film which shows excellent alkali resistance. For example, even when an alkali substance adheres to the surface of the gas detection element, corrosion by the alkali substance can be prevented.

Further, the oxide film is impermeable to gas (formed densely), thereby restraining entry, into the oxide film, of impurities (e.g., organic silicon) contained in an environmental atmosphere which contains gas-to-be-detected. For example, when the oxide film has a porous structure, which is permeable to gas, impurities are likely to adhere to the oxide film through entry into pores. The present invention, however, is free from such adhesion.

Thus, a change in thermal capacity of the gas detection element can be restrained, which could otherwise result from entry of impurities into the outermost surface layer of the gas detection element. Therefore, the output of the gas detection element is stabilized and becomes accurate. That is, high detection accuracy can be attained.

Preferably, the surface of the insulation layer is of silicon nitride. Since silicon nitride has excellent corrosion resistance and stability, the durability of the gas detection element can be enhanced in combination with excellent alkali resistance being attained through provision of the oxide film.

In order to restrain the generation of holes (spots and pores) in the gas impermeable oxide film, the oxide film must have a minimal thickness. The gas impermeable oxide film can be formed in such a manner as to have a thickness equal to or greater than one-twentieth of a thickness of the heat-generating resistor as measured in a direction perpendicular to front and back surfaces of the semiconductor substrate.

More specifically, the gas impermeable oxide film can be formed in such a manner as to have a thickness of 20 nm to 500 nm inclusive. When the thickness of the gas impermeable oxide film is excessively large, the flexibility of the gas impermeable oxide film toward thermal expansion and contraction reduces. Thus, preferably, the upper limit of the thickness of the gas impermeable oxide film is specified to be 500 nm.

Preferably, the thickness of the gas impermeable oxide film is a distance between the surface of the insulation layer and a surface of the gas impermeable oxide film which comes into contact with the gaseous atmosphere.

This means the following: as viewed at any point on the surface of the insulation layer, the thickness of the gas impermeable oxide film conforms to the thickness range of 20 nm to 500 nm inclusive. In other words, the surface of the insulation layer has irregularities to a certain extent stemming from the existence of the heat-generating resistor within the insulation layer, and the gas impermeable oxide film is formed in such a manner as to have a thickness of 20 nm to 500 nm inclusive as measured along the irregular surface profile. Thus, the distance from an edge of the irregular surface profile of the insulation layer to the surface of the oxide film reliably falls within the required range, thereby preventing variation in the effect of provision of the oxide film, which could otherwise result from the irregularities.

The gas impermeable oxide film can be formed by a sputtering method.

According to the sputtering method, ions are caused to impinge on a desired material so as to eject particles of the material, and the ejected particles adhere to a target, thereby forming a desired thin film on the target. By use of the sputtering method, a denser film can be formed.

The gas detector of the present invention can yield the aforementioned effect (i.e., the effect of attaining high detection accuracy) when the gas detection element is a thermal-conductivity-type gas detection element or a catalytic-combustion-type gas detection element.

Particularly, the thermal-conductivity-type gas detection element is conceived to take greater advantage of the effect of provision of the gas impermeable oxide film. That is, gas-to-be-detected is very low in thermal conductivity. Also, in order to detect gas-to-be-detected having a low concentration on the order of ppm (parts per million), the output of the gas detection element must be amplified. Thus, if the output of the gas detection element involves an error, the error is enlarged. Therefore, the smaller the error, the better. In this regard, the present invention is advantageous, since the present invention can restrain a change in thermal capacity, which could otherwise result from entry of impurities, and thus can restrain error.

The gas detector of the present invention may be configured to detect hydrogen gas and thus is suitable for practical use.

More specifically, the gas detector can be configured such that at least the gas detection element is disposed at a predetermined position on a fuel cell apparatus for generating electricity from hydrogen and oxygen, and is adapted to detect hydrogen gas used in the fuel cell apparatus.

DETAILED DESCRIPTION OF THE INVENTION

An embodiment of the present invention will next be described with reference to the drawings.

Figure 1:
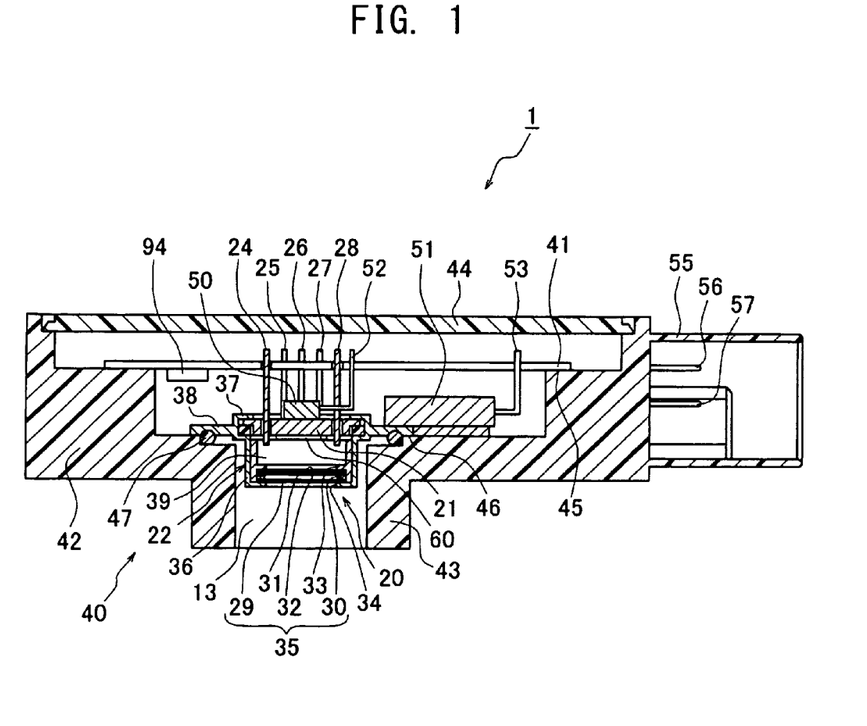
FIG. 1 is a longitudinal sectional view showing a gas detector 1 according to an embodiment of the present invention.

FIG. 1 is a longitudinal sectional view showing a gas detector 1 to which the present invention is applied. The gas detector 1 is used, for example, to detect leakage of hydrogen gas used in a fuel cell apparatus for generating electricity from hydrogen and oxygen.

The gas detector 1 includes an element case 20 and a housing case 40, which supports the element case 20.

Also, the gas detector 1 has a gas detection element 60, which is a thermal-conductivity-type gas detection element, and a circuit board 41, which is electrically connected to the gas detection element 60. A microcomputer 94 is mounted on the circuit board 41.

The gas detection element 60 is accommodated in the element case 20. The circuit board 41, together with the element case 20, is accommodated in the housing case 40.

First, the structure of the housing case 40 will be described.

The housing case 40 includes a case body 42 and a case cover 44, which covers an upper end opening of the case body 42.

The case body 42 is a container which has openings at the upper and lower sides, respectively, and has a predetermined height. The case body 42 includes a circuit board holder portion 45 for holding a peripheral portion of the circuit board 41, and a holder portion 46 for holding a flange portion 38 of the element case 20.

The case body 42 also includes a flow path formation portion 43 formed at the lower center thereof and a connector 55 formed at a side portion thereof and adapted to receive electricity supplied from the outside.

The flow path formation portion 43 accommodates an inlet portion 35 of the element case 20 through which gas-to-be-detected is introduced into and ejected from the element case 20. In this manner, the element case 20 is held by the holder portion 46 while being accommodated within the housing case 40. A seal member 47 is disposed between the case body 42 and the flange portion 38 of the element case 20 for sealing the gap therebetween.

The connector 55 is adapted to supply electricity to the circuit board 41 (and the microcomputer 94) and is mounted to the outer side surface of the case body 42. The connector 55 internally has a plurality of connector pins 56 and 57 projecting from the side wall of the case body 42. The connector pins 56 and 57 are electrically connected to the circuit board 41 (and the microcomputer 94) via respective wiring lines (not illustrated) embedded in the side wall of the case body 42.

Next, the element case 20 is described.

The element case 20 includes a connection terminal block 21, on which the gas detection element 60 is mounted, and a detection space formation member 22, which has a cylindrical wall adapted to nip a peripheral portion of the connection terminal block 21 and projecting toward a gas inlet 13 through which gas-to-be-detected is introduced. A seal member (not shown) is disposed at a peripheral portion of the connection terminal block 21 of the element case 20 for sealing the gap between the connection terminal block 21 and the detection space formation member 22. A space enclosed by the connection terminal block 21 and the detection space formation member 22 is a detection space 39 into which gas-to-be-detected is introduced.

The connection terminal block 21 has insertion holes through which connection terminals 24 to 28 are inserted respectively. Peripheral portions around the insertion holes are covered with an electrically insulative member.

The connection terminals 24 to 28 are electrically conductive rodlike members for electrically connecting the gas detection element 60 to circuits formed on the circuit board 41.

The detection space formation member 22 includes a sheath 36; a terminal block support portion 37, which nips a peripheral portion of the connection terminal block 21; and the flange portion 38, which is supported by the holder portion 46 of the housing case 40. The detection space formation member 22 has an inlet 34 formed at its lower end portion. The inlet 34 is an opening through which gas-to-be-detected is introduced into the detection space 39.

The inlet portion 35 is provided in the vicinity of the inlet 34. The inlet portion 35 forms a flow path through which gas-to-be-detected is introduced toward the gas detection element 60 and ejected. The inlet portion 35 is fitted, from a side toward the inlet 34, with a water repellent filter 29, a spacer 30, and two metallic meshes 31 and 32. These members are fixedly sandwiched between the detection space formation member 22 and a filter fixation member 33.

The water repellent filter 29 is located closest to the inlet 34. The water repellent filter 29 is a water repellent thin film for eliminating water droplets contained in gas-to-be-detected. By virtue of the water repellent filter 29, even in a very humid environment where water droplets and the like are flying, adhesion of water to the gas detection element 60 can be prevented. The water repellent filter 29 may be the type to eliminate water droplets through physical adsorption. The water repellent filter 29 can be formed by use of, for example, polytetrafluoroethylene (PTFE).

The spacer 30 is disposed on the inner circumferential wall of the filter fixation member 33 and has an opening through which gas-to-be-detected is introduced (a ring-shaped member as viewed in plane). The spacer 30 has a predetermined thickness for adjusting the relative position between the water repellent filter 29 and the two metallic meshes 31 and 32.

Each of the two metallic meshes 31 and 32 has a predetermined thickness and predetermined openings. The two metallic meshes 31 and 32 function as a flame arrester for preventing outward ejection of flame even when hydrogen gas contained in gas-to-be-detected ignites as a result of the temperature of the heat-generating resistor of the gas detection element 60 rising above the ignition temperature of hydrogen gas.

The filter fixation member 33 has a cylindrical wall in contact with the inner wall surface of the detection space formation member 22, as well as a protrusion protruding radially inward from the inner surface of the cylindrical wall. The protrusion and the detection space formation member 22 fixedly sandwich the water repellent filter 29, the spacer 30, and the two metallic meshes 31 and 32 therebetween.

Next, the circuit board 41 is described.

The circuit board 41 is a plate-like substrate having a predetermined thickness and bears a control circuit 90 (which will be described later) for detecting flammable gas contained in gas-to-be-detected, and a temperature control circuit (not shown) for controlling the temperature of heat-generating elements 50 and 51.

The control circuit 90 on the circuit board 41 is electrically connected to the gas detection element 60 by means of the connection terminals 24 to 28. The temperature control circuit on the circuit board 41 is electrically connected to the heat-generating elements 50 and 51 by means of lead wires 52 and 53.

The microcomputer 94 mounted on the circuit board 41 executes a process of computing the concentration of flammable gas contained in gas-to-be-detected on the basis of output of the control circuit 90 provided on the circuit board 41 (sensor output computation process). Also, the microcomputer 94 executes a process of controlling the amount of heat generation (temperature) of the heat-generating elements 50 and 51 on the basis of output of the temperature control circuit (temperature control process). The microcomputer 94 comprises of, at least, a memory for storing programs for executing the sensor output computation process and the temperature control process for the heat-generating elements 50 and 51, and a CPU for executing the programs stored in the memory.

Next, the heat-generating elements 50 and 51 are described.

The heat-generating elements 50 and 51 are adapted to heat the element case 20 to thereby maintain the temperature of the inner surface of the element case 20 or the temperature of the detection space 39 at a temperature higher than a predetermined temperature (at a temperature higher than at least the dew point). The heat-generating elements 50 and 51 are formed by use of, for example, a resistor used in an electronic component or the like, or a film heater. Heating by the heat-generating elements 50 and 51 prevents gas-to-be-detected from being cooled on the inner surface of the element case 20 or in the detection space 39, thereby preventing dew condensation on the inner surface of the element case 20 or in the detection space 39 or preventing the temperature of gas-to-be-detected from becoming unstable.

Next, the outline of the control circuit 90 is described with reference to FIG. 2.

Figure 2:
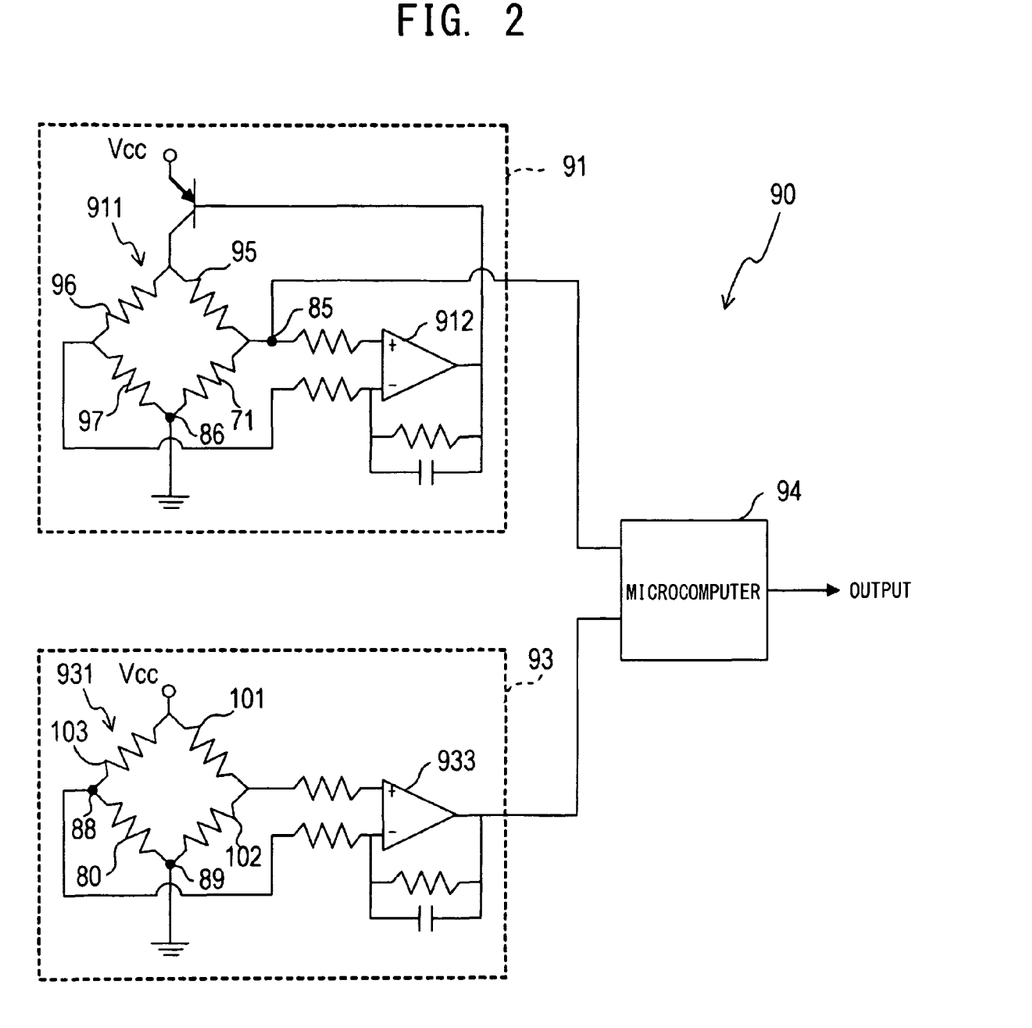
FIG. 2 is a diagram showing a control circuit 90 provided on a circuit board 41.

As shown in FIG. 2, the control circuit 90 has a gas detection circuit 91 and a temperature-measuring circuit 93.

The gas detection circuit 91 has a Wheatstone bridge 911 consisting of a heat-generating resistor 71 provided in the gas detection element 60 and fixed resistors 95, 96, and 97 provided on the circuit board 41, and an operational amplifier 912 provided on the circuit board 41 and adapted to amplify a potential difference obtained from the Wheatstone bridge 911.

In the case of using the heat-generating resistor 71 whose resistance increases with its own temperature, the operational amplifier 912 operates as follows: when the temperature of the heat-generating resistor 71 increases, the operational amplifier 912 lowers its output voltage so as to maintain the heat-generating resistor 71 at a predetermined temperature; and when the temperature of the heat-generating resistor 71 lowers, the operational amplifier 912 increases its output voltage.

Since output of the operational amplifier 912 is connected to the Wheatstone bridge 911, when the temperature of the heat-generating resistor 71 rises above a predetermined temperature, the output voltage of the operational amplifier 912 lowers in order to lower the temperature of the heat-generating resistor 71, so that voltage applied to the Wheatstone bridge 911 lowers. At this time, voltage of an electrode 85, which serves as an end portion of the Wheatstone bridge 911, is detected as output of the gas detection circuit 91 by the microcomputer 94. The output value detected by the microcomputer 94 is used in the computation process for detecting flammable gas contained in gas-to-be-detected.

The temperature-measuring circuit 93 has a Wheatstone bridge 931 comprising a temperature-measuring resistor 80 (which will be described later) provided in the gas detection element 60 and fixed resistors 101, 102, and 103 provided on the circuit board 41, and an operational amplifier 933 provided on the circuit board 41 and adapted to amplify a potential difference obtained from the Wheatstone bridge 931. Output of the operational amplifier 933 is detected by the microcomputer 94. The output value detected by the microcomputer 94 is used for measuring the temperature of gas-to-be-detected and in the computation process for detecting flammable gas contained in gas-to-be-detected.

On the basis of the output value of the control circuit 90 having the above-mentioned configuration, the microcomputer 94 computes the concentration of flammable gas as follows. First, the CPU (not shown) of the microcomputer 94 executes a program stored in the memory (not shown) of the microcomputer 94 by use of the output value of the gas detection circuit 91, thereby outputting a first output value substantially proportional to the concentration of flammable gas. Since the first output value involves an output variation stemming from variation in temperature of atmosphere in the detection space 39, subsequently, the CPU outputs a second output value obtained by correcting the first output value on the basis of output from the temperature-measuring circuit 93. Further, the CPU of the microcomputer 94 outputs the concentration of flammable gas contained in gas-to-be-detected on the basis of the relation between the second output value and the concentration of flammable gas which is stored in the memory (not shown) of the microcomputer 94. In this manner, the first output value is corrected on the basis of output of the temperature-measuring circuit 93. Therefore, flammable gas can be detected with accuracy. The process of computing the concentration of flammable gas is not limited to that mentioned above, but publicly known computation means may be used as appropriate.

Figure 3:
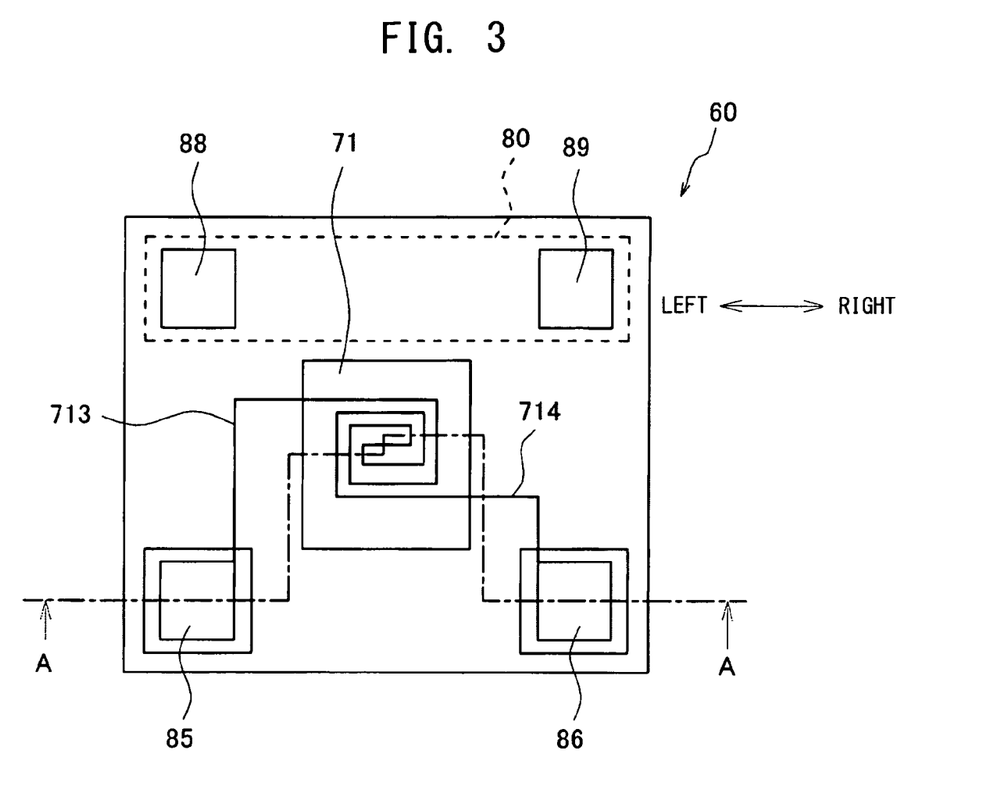
FIG. 3 is a plan view showing a gas detection element 60.
Figure 4:
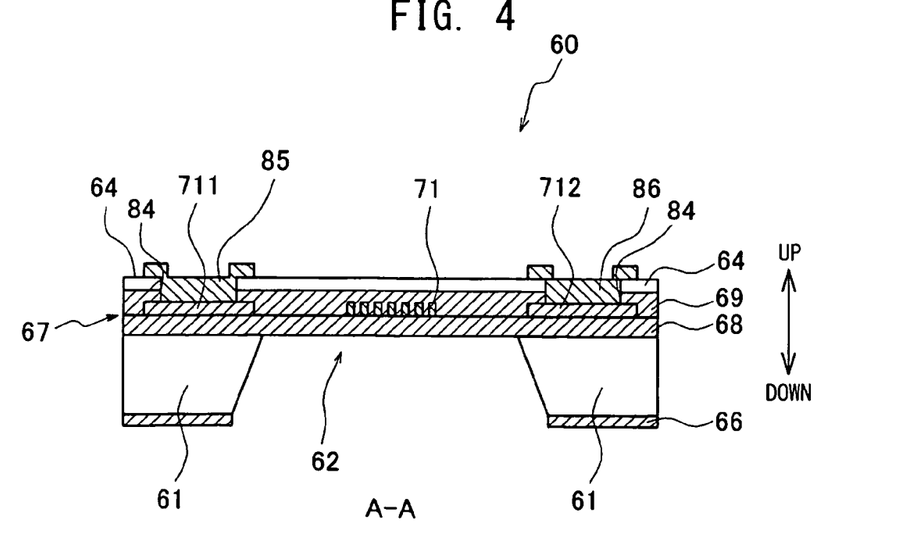
FIG. 4 is a sectional view of the gas detection element 60 taken along line A-A of FIG. 3.

Next, the composition of the gas detection element 60 is described. FIG. 3 is a plan view showing the gas detection element 60. FIG. 4 is a sectional view (taken along line A-A of FIG. 3) showing the gas detection element 60. In the plan view of FIG. 3, the horizontal direction on the paper on which FIG. 3 appears is referred to as the horizontal direction of the plan view. In the sectional view of FIG. 4, the vertical direction on the paper on which FIG. 4 appears is referred to as the vertical direction of the sectional view.

The gas detection element 60 is manufactured by use of the micromachining technique. As shown in FIG. 4, the gas detection element 60 has a semiconductor substrate 61 of silicon, and insulation layers (an upper insulation layer 67 and a lower insulation layer 66) provided on the upper and lower sides, respectively, of the semiconductor substrate 61. The upper insulation layer 67 is formed on the front side of the semiconductor substrate 61 of silicon, and the lower insulation layer 66 is formed on the back side of the semiconductor substrate 61. Also, a protection layer 64 is formed on the surface of the upper insulation layer 67. The upper insulation layer 67 consists of an insulation layer 68 formed on the front side of the semiconductor substrate 61 of silicon, and an insulation protection layer 69 formed on the surface of the insulation layer 68. The gas detection element 60 also has the heat-generating resistor 71.

The semiconductor substrate 61 of silicon has a cavity 62 formed in a region located under the heat-generating resistor 71. The cavity 62 is formed by removing a portion of the semiconductor substrate 61 of silicon in such a manner as to form an opening. A portion of the upper insulation layer 67 is exposed to the cavity 62 from above. The heat-generating resistor 71 is embedded in the upper insulation layer 67 in a region corresponding to the cavity 62.

By virtue of the above configuration, the heat-generating resistor 71 is heat-insulated from the surrounding by means of the cavity 62. Thus, the heat-generating resistor 71 raises and lowers temperature in a short period of time. Therefore, the thermal capacity of the gas detection element 60 can be reduced.

Wiring films 711 and 712 are formed on the same plane as that on which the heat-generating resistor 71 is formed. The wiring films 711 and 712 and wiring lines 713 and 714 (for the wiring lines 713 and 714, see FIG. 3) are embedded in the upper insulation layer 67. The upper insulation layer 67 is formed from an electrically insulative material, for example, silicon oxide ($SiO_2$) or silicon nitride ($Si_3N_4$). The upper insulation layer 67 may be formed such that a plurality of layers are formed from the same material or such that a plurality of layers are formed from different materials. In the present embodiment, at least the insulation protection layer 69 is formed from silicon nitride ($Si_3N_4$).

The protection layer 64 is formed with a predetermined thickness on the upper surface of the upper insulation layer 67 and is formed from, for example, alumina or silicon oxide. The protection layer 64 is provided in such a manner as to cover the heat-generating resistor 71, the wiring films 711 and 712, and the wiring lines 713 and 714 for preventing contamination and damage thereof.

The heat-generating resistor 71 is formed spirally (see FIG. 3) and varies in temperature and resistance according to the temperature of gas-to-be-detected (more specifically, thermal conduction to flammable gas). The heat-generating resistor 71 is formed from an electrically conductive material having a high temperature coefficient of resistance, for example, platinum (Pt). In the case of detecting hydrogen gas, which is a flammable gas, the amount of heat removed by the heat-generating resistor 71 through thermal conduction to hydrogen gas corresponds to the concentration of hydrogen gas. Therefore, the concentration of hydrogen gas can be detected on the basis of a change in electrical resistance of the heat-generating resistor 71.

Notably, the temperature of gas-to-be-detected has an effect on a change in resistance of the heat-generating resistor 71. Thus, by use of temperature detected on the basis of electric resistance of the temperature-measuring resistor 80 (FIG. 3), which will be described later, the concentration of gas-to-be-detected which is detected on the basis of a change in electric resistance of the heat-generating resistor 71 is corrected, whereby accuracy in detecting the concentration of gas-to-be-detected can be improved.

Next, the left end of the heat-generating resistor 71 is electrically connected to the electrode 85 (FIG. 3) via the wiring line 713 (FIG. 3) and the wiring film 711 (FIG. 4), which are embedded in the upper insulation layer 67 (FIG. 4) and are integrally formed with the heat-generating resistor 71. The right end of the heat-generating resistor 71 is electrically connected to a ground electrode 86 (FIG. 3) via the wiring line 714 (FIG. 3) and the wiring film 712 (FIG. 4), which are embedded in the upper insulation layer 67 and are integrally formed with the heat-generating resistor 71. The electrode 85 and the ground electrode 86 are terminals for external connection of the wiring lines connected to the heat-generating resistor 71 and are exposed through respective contact holes 84 (FIG. 4). The electrode 85 and the ground electrode 86 are formed from, for example, aluminum (Al) or gold (Au).

The temperature-measuring resistor 80 (FIG. 3) is adapted to detect the temperature of gas-to-be-detected existing in the detection space 39 (see FIG. 1). The temperature-measuring resistor 80 is formed between the upper insulation layer 67 (FIG. 4) and the protection layer 64 (FIG. 4) and on a plane in parallel with the semiconductor substrate 61 of silicon. The temperature-measuring resistor 80 is formed from a metal whose electric resistance varies in proportion to temperature, for example, platinum (Pt).

The temperature-measuring resistor 80 is electrically connected to an electrode 88 (FIG. 3) and a ground electrode 89 (FIG. 3). The electrode 88 and the ground electrode 89 are exposed through respective contact holes (not shown). The electrode 88 and the ground electrode 89 are formed from, for example, aluminum (Al) or gold (Au).

Next, a process of manufacturing the gas detection element 60 is described with reference to FIGS. 5A to 5F.

Figure 5A:
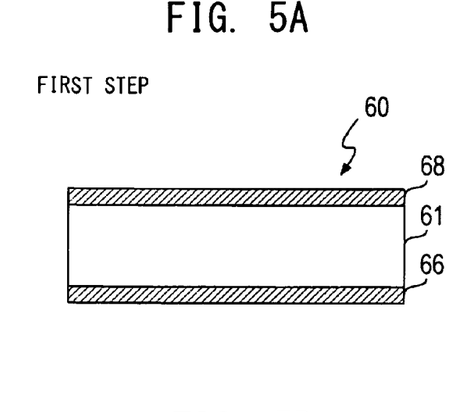
FIGS. 5A to 5F are views showing steps of manufacturing the gas detection element 60.

(1) Step of forming the insulation layer 68 and the lower insulation layer 66 (first step):

The semiconductor substrate 61 of silicon is prepared. The semiconductor substrate 61 of silicon is cleaned and then subjected to a thermal oxidation process. By this process, a silicon oxide film ($SiO_2$ film) having a thickness of 100 nm is formed on each of the front and back surfaces of the semiconductor substrate 61 of silicon. Then, a silicon nitride film ($Si_3N_4$ film) having a thickness of 200 nm is formed, by a low-pressure CVD process, on each of the silicon oxide films formed on the upper and lower sides of the semiconductor substrate 61 of silicon.

By this procedure, the silicon oxide film and the silicon nitride film formed on the upper side of the semiconductor substrate 61 of silicon collectively serve as the insulation layer 68, and the silicon oxide film and the silicon nitride film formed on the lower side of the semiconductor substrate 61 of silicon collectively serve as the lower insulation layer 66.

Figure 5B:
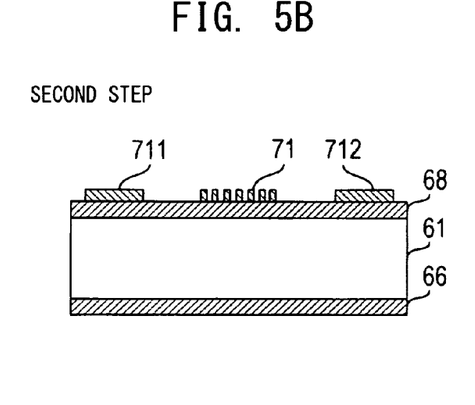

(2) Step of forming the heat-generating resistor 71 and the wiring films 711 and 712 (second step):

After the insulation layer 68 and the lower insulation layer 66 are formed as mentioned above, in an atmosphere having a temperature of 300° C., a tantalum film (Ta film) having a thickness of 20 nm is formed on the surface of the insulation layer 68 by a sputtering method. Next, a platinum film (Pt film) having a thickness of 400 nm is formed on the tantalum film in an overlaying manner by a sputtering method; and then, a tantalum film having a thickness of 20 nm is again formed on the platinum film in an overlaying manner by a sputtering method. The tantalum films are adapted to enhance adhesion strength between the platinum film and the insulation layer 68.

Subsequently, by a photolithographic process, portions of the tantalum films and the platinum film which do not correspond to the heat-generating resistor 71 and the wiring films 711 and 712 are etched away. By this process, the heat-generating resistor 71 and the wiring films 711 and 712 are formed on the surface of the insulation layer 68. The wiring films 711 and 712 and the heat-generating resistor 71 have a temperature coefficient of resistance of about 2,000 ppm/° C. In this step, the temperature-measuring resistor 80 is also formed on the surface of the insulation layer 68 by a method similar to that used to form the heat-generating resistor 71.

Figure 5C:
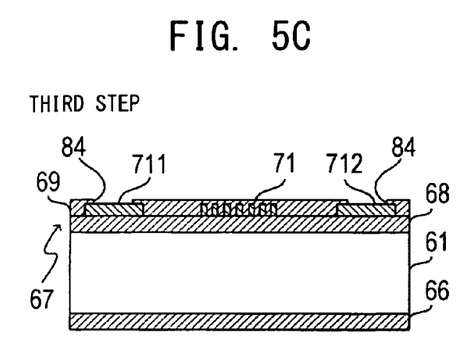

(3) Step of forming the insulation protection layer 69 (third step):

After the heat-generating resistor 71 and the wiring films 711 and 712 are formed as mentioned above, a silicon oxide layer ($SiO_2$ layer) having a thickness of 100 nm is formed on the surface of the insulation layer 68 by a plasma CVD process in such a manner as to cover the heat-generating resistor 71 and the wiring films 711 and 712. Further, on the silicon oxide layer, a silicon nitride layer ($Si_3N_4$ layer) having a thickness of 200 nm is formed in an overlaying manner by a low-pressure CVD process. The processes for forming these layers are carried out at a temperature lower than that for the processes for forming the insulation layer 68, the lower insulation layer 66, and the wiring films 711 and 712.

Next, portions of the silicon nitride layer and the silicon oxide layer which correspond to the wiring films 711 and 712 are etched away by a photolithographic process. By this process, the insulation protection layer 69 having the contact holes 84 is formed on the surface of the insulation layer 68 in such a manner as to cover the heat-generating resistor 71. Also, by a similar etching process, contact holes (not shown) for the temperature-measuring resistor 80 are formed.

Figure 5D:
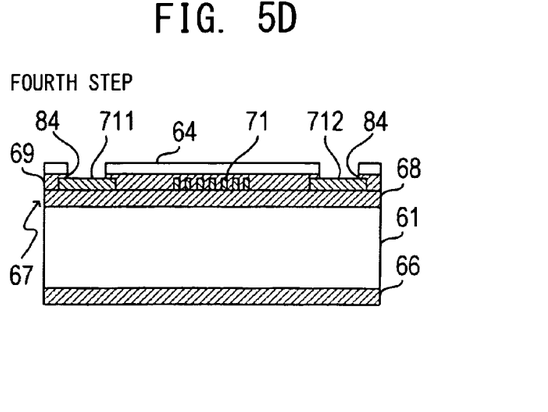

(4) Step of forming the protection layer 64 (fourth step):

After the insulation protection layer 69 is formed as mentioned above, an alumina layer having a thickness of 20 nm is formed in an overlaying manner by a sputtering method.

Then, portions of the alumina layer which correspond to the wiring films 711 and 712 are etched away by a photolithographic process.

Figure 5E:
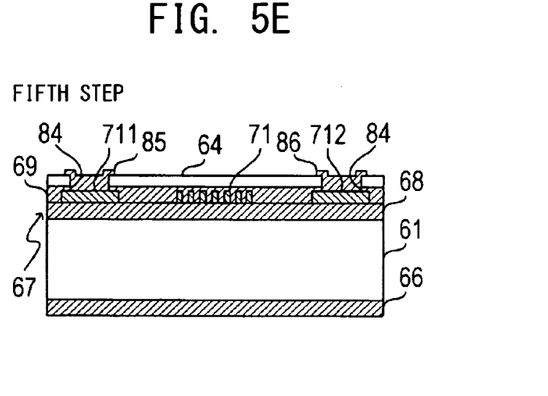

(5) Step of forming the electrodes 85 and 86 (fifth step):

After the protection layer 64 is formed as mentioned above, a chromium film (Cr film) having a thickness of 20 nm is formed in an overlaying manner on the protection layer 64 by a sputtering method. Then, a gold film (Au film) having a thickness of 600 nm is formed on the chromium film in an overlaying manner by a sputtering method.

Subsequently, portions of an electrode layer consisting of the gold film and the chromium film which do not correspond to the contact holes 84 are etched away by a photolithographic process. By this procedure, the electrodes 85 and 86 are formed in and around the respective contact holes 84. In this step, the electrode 88 and the ground electrode 89 are also formed in and around the respective unillustrated contact holes.

Figure 5F:
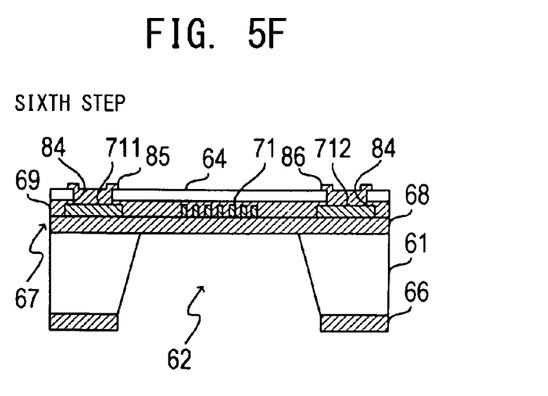

(6) Step of forming the cavity 62 (sixth step):

After the electrodes 85 and 86 are formed as mentioned above, a portion of the lower insulation layer 66 which corresponds to the heat-generating resistor 71 is etched away. Then, a portion of the semiconductor substrate 61 of silicon which corresponds to the etched-away portion is etched away by use of tetramethylammonium hydroxide, thereby exposing a portion of the insulation layer 68 which corresponds to the heat-generating resistor 71. By this procedure, the cavity 62 is formed in portions of the semiconductor substrate 61 of silicon and the lower insulation layer 66 which correspond to the heat-generating resistor 71.

Meanwhile, the "thickness" of the protection layer 64 is described with reference to FIG. 6.

Figure 6:
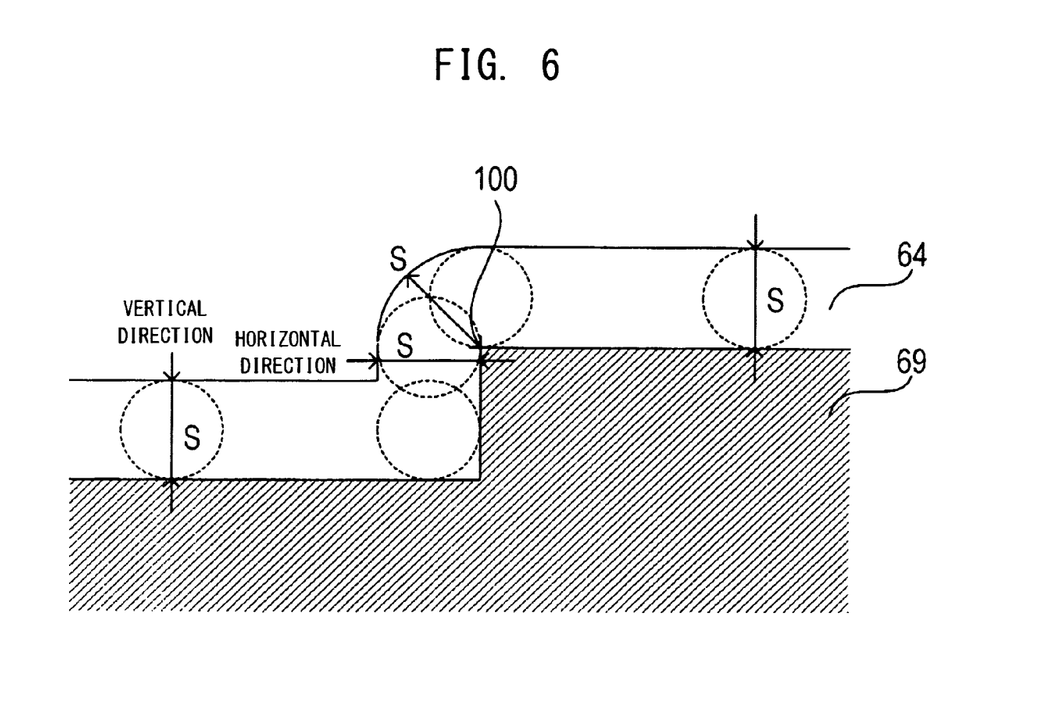
FIG. 6 is a view for explaining a definition of the thickness of a protection layer 64.

As a premise, the surface of the insulation protection layer 69 is rugged (uneven) as shown in FIG. 6, since the heat-generating resistor 71, for example, exists under the surface.

For example, that the protection layer 64 has a thickness of S nm means that the trajectory of a circle having a diameter of S resulting from the circle rolling on the surface of the insulation protection layer 69 is contained on the inside of the surface of the protection layer 64. That is, as shown in FIG. 6, both the thickness along the vertical direction and the thickness along the horizontal direction are S nm. Further, the thickness from an edge 100 of the insulation protection layer 69 (the distance from the edge 100 to the surface of the protection layer 64) is also S nm.

Figure 7:
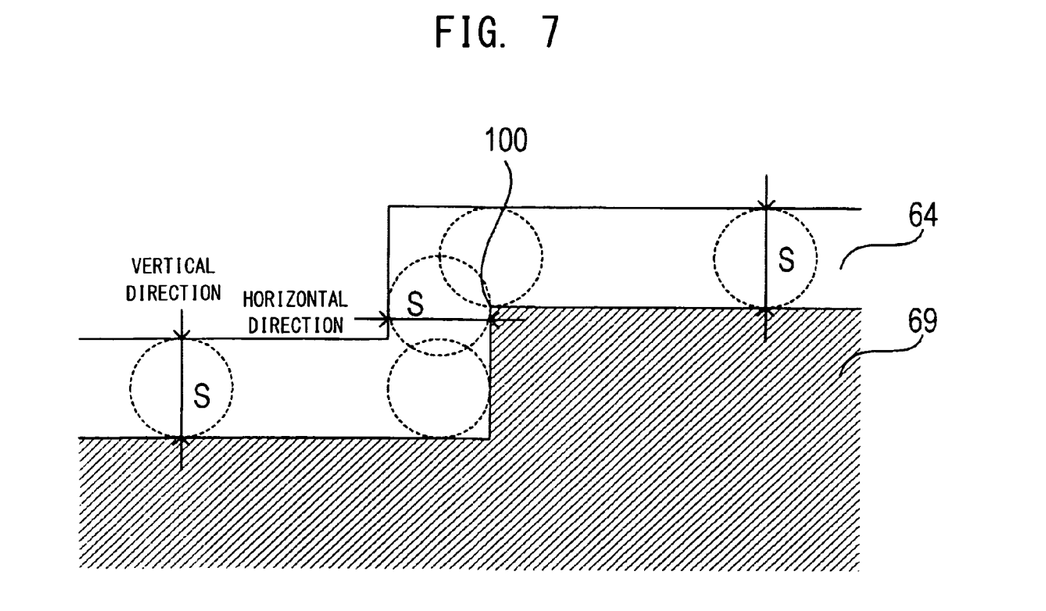
FIG. 7 is a view for explaining another definition of the thickness of the protection layer 64.

As shown in FIG. 7, the rugged surface of the protection layer 64 may have an edge corresponding to an edge of the rugged surface of the insulation protection layer 69.

In the present embodiment, since the surface of the gas detection element 60 is covered with the protection layer 64 of alumina, the gas detection element 60 has excellent alkali resistance. Further, since the protection layer 64 is formed by a sputtering method, the protection layer 64 is very dense (impermeable to gas, for example). Therefore, as compared with, for example, the case where the protection layer 64 has a porous structure, there can be restrained the entry, into the protection layer 64, of impurities (e.g., organic silicon) contained in an environmental atmosphere which contains gas-to-be-detected.

Next will be described the experiments conducted by the applicant of the present application for verifying the effects of the present invention.

Experiment 1

Organic Silicon Compound Poisoning Test

Outline of Experiment

Figure 8:
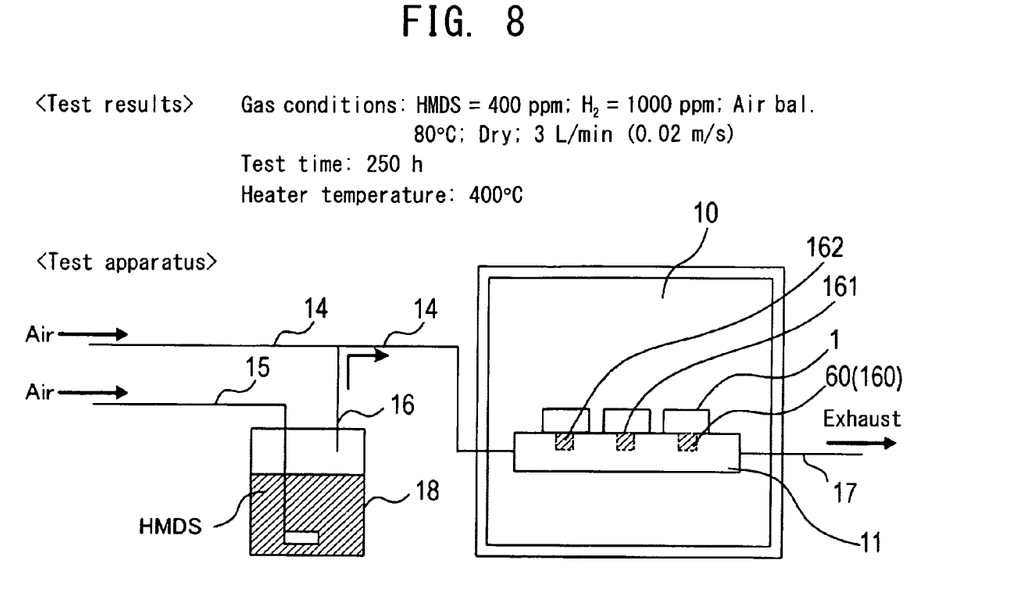
FIG. 8 is a view showing the outline of Experiment 1.

FIG. 8 shows the outline of Experiment 1. In the present Experiment 1, the gas detection element 60 of the gas detector 1 to which the present invention is applied (hereinafter, referred to as an alumina-sputtered protection layer element 160), a gas detection element whose protection layer 64 is formed through alumina sol being spin-coated (hereinafter, referred to as an alumina-sol protection layer element 161), and a gas detection element not having the protection layer 64 (hereinafter, referred to as a bare element 162) were prepared and verified.

In FIG. 8, a constant-temperature oven 10 is a container whose inner temperature is held at 80° C. A chamber 11 is disposed within the constant-temperature oven 10.

Piping 14 and piping 17 are connected to the chamber 11. The gas detector 1 is disposed such that its gas detection element 60 (the alumina-sputtered protection layer element 160) is accommodated within the chamber 11. In this manner, the gas detectors 1 having the alumina-sputtered protection layer element 160, the alumina-sol protection layer element 161, and the bare element 162, respectively, are disposed such that the alumina-sputtered protection layer element 160, the alumina-sol protection layer element 161, and the bare element 162 are accommodated within the chamber 11.

Air is introduced toward the chamber 11 through the piping 14 connected to the chamber 11. Gas contained in a container 18, which will be described later, is led to a midway point of the piping 14 and merges with air. The piping 17 allows gas to be exhausted from the interior of the chamber 11 to the exterior of the chamber 11.

The container 18 is disposed externally of the constant-temperature oven 10 and contains HMDS (adhesion-improving application solution), which is an organic silicon compound. Air is introduced into the container 18 through piping 15. The gas contained in the container 18 is introduced into the piping 14 through piping 16.

By means of the above configuration, a mixed gas consisting of 400 ppm HMDS and 1,000 ppm $H_2$ is generated and introduced into the chamber 11. The flow rate of the mixed gas is 3 L/min (velocity 0.02 m/s).

The heat-generating resistors 71 of the gas detection elements are held at a temperature of 400° C.

In the present Experiment 1, while the mixed gas was kept flowing for 250 hours, voltages (hereinafter, referred to as heater voltages) applied to the heat-generating resistors 71 of the gas detection elements were detected.

Experiment Results and Consideration

Figure 9:
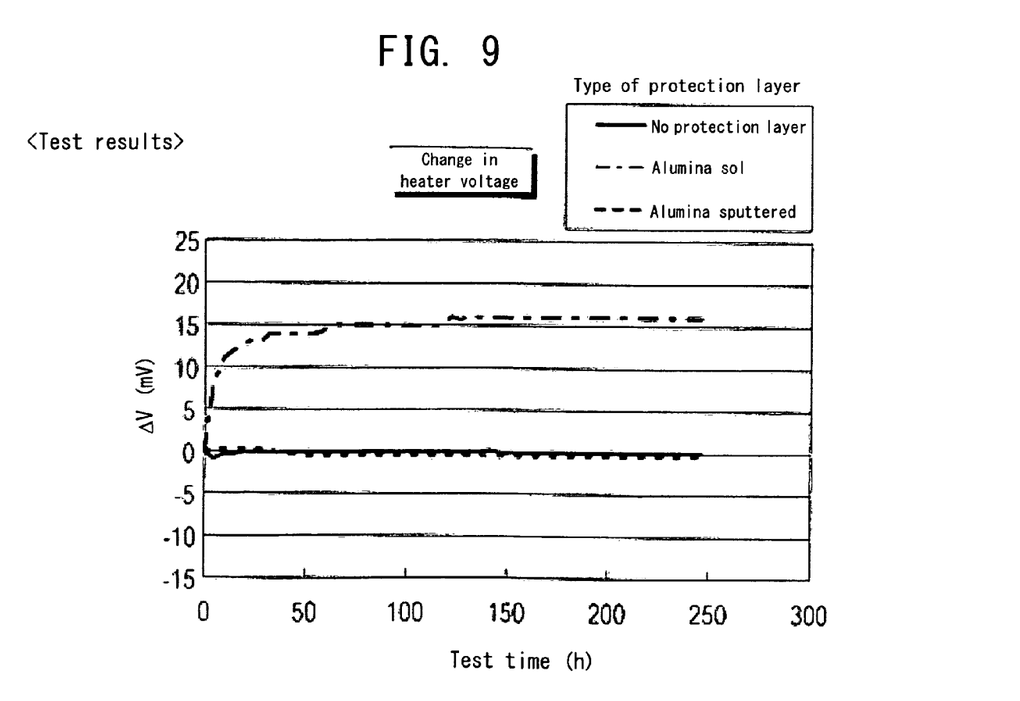
FIG. 9 is a graph showing the results of Experiment 1.

FIG. 9 is a graph showing a change in heater voltage with time of each of the gas detection elements (the alumina-sputtered protection layer element 160, the alumina-sol protection layer element 161, and the bare element 162).

Figure 10:
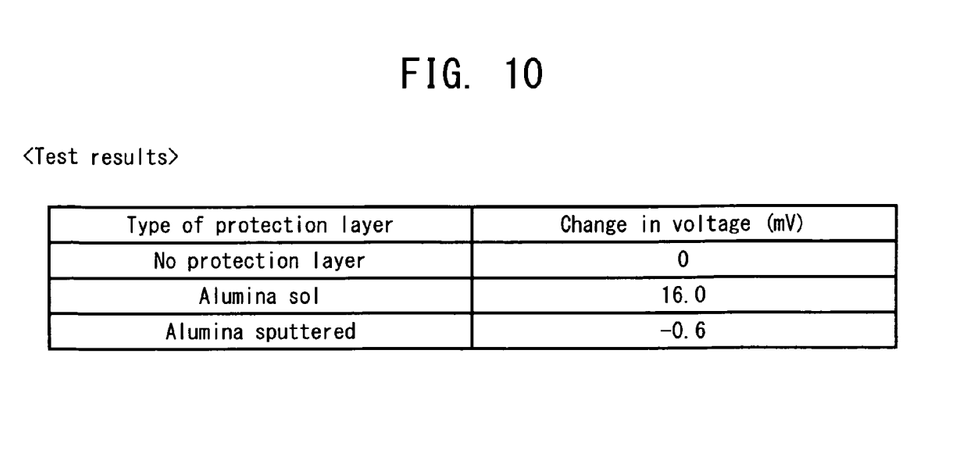
FIG. 10 is a table showing the results of Experiment 1.

FIG. 10 shows a change in heater voltage of each of the gas detection elements. More specifically, the change in heater voltage is the difference between a heater voltage as measured at start of the test and a heater voltage as measured after the elapse of 250 hours from start of the test. In FIGS. 9 and 10, the term "alumina sputtered" corresponds to the alumina-sputtered protection layer element 160; the term "alumina sol" corresponds to the alumina-sol protection layer element 161; and the term "no protection layer" corresponds to the bare element 162. This also applies to FIG. 12, which will be described later.

As shown in FIGS. 9 and 10, the alumina-sputtered protection layer element 160 and the bare element 162 show almost no change in heater voltage with the elapse of time. Specifically, the alumina-sputtered protection layer element 160 shows a change in heater voltage of −0.6 mV between the time of start of the test and the time after the elapse of 250 hours from start of the test. The bare element 162 shows a change in heater voltage of 0 mV between the time of start of the test and the time after the elapse of 250 hours from start of the test. Thus, the alumina-sputtered protection layer element 160 and the bare element 162 are found to have almost no change in thermal capacity, indicating the amount of adhesion of organic silicon is very small.

By contrast, the alumina-sol protection layer element 161 shows a great increase in heater voltage. More specifically, a change in heater voltage is 16 mV between the time of start of the test and the time after the elapse of 250 hours from start of the test. Thus, the alumina-sol protection layer element 161 is found to involve a great increase in thermal capacity, indicating adhesion of a large amount of organic silicon.

Thus, it has been confirmed from the above experiment results that, in the gas detection element 60 of the present embodiment, adhesion of impurities (organic silicon) can be restrained, and thus a change in thermal capacity can be restrained. Therefore, the gas detection element 60 provides stable and accurate output. In other words, the gas detection element 60 exhibits high detection accuracy.

Thus, in the present invention, the protection layer 64 which brings about a change in heater voltage which falls within a range of ±5 mV as measured in the above predetermined test period of time can be defined as a gas impermeable protection layer.

Experiment 2

Alkali Resistance Test

Outline of Experiment

Figure 11:
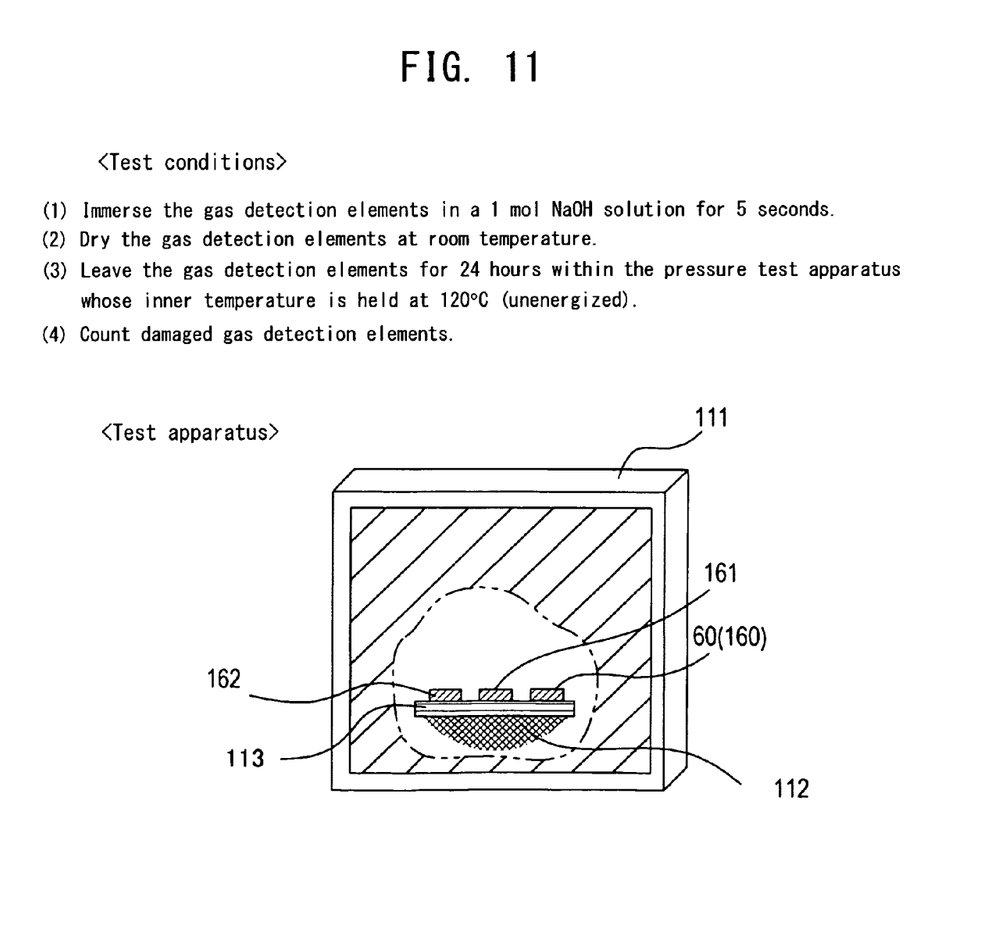
FIG. 11 is a view showing the outline of Experiment 2.

FIG. 11 shows the outline of Experiment 2. Similar to Experiment 1, the alumina-sputtered protection layer element 160, the alumina-sol protection layer element 161, and the bare element 162 were prepared and verified.

First, a solution which contains 1 mol sodium hydroxide (NaOH) (hereinafter, referred to as the NaOH solution) was prepared. The gas detection elements (the alumina-sputtered protection layer element 160, the alumina-sol protection layer element 161, and the bare element 162) were immersed in the NaOH solution for 5 sec.

Then, the gas detection elements were dried at room temperature.

Subsequently, the dried gas detection elements (the alumina-sputtered protection layer element 160, the alumina-sol protection layer element 161, and the bare element 162) were placed in a pressure test apparatus 111 and were left for 24 hours in the pressure test apparatus 111 whose inner temperature was held at 120° C.

A total of 54 gas detection elements, 18 pieces each of the alumina-sputtered protection layer element 160, the alumina-sol protection layer element 161, and the bare element 162, were prepared and placed in the pressure test apparatus 111.

The pressure test apparatus 111 contains a table 113 on which the gas detection elements are placed. A space under the table 113 is filled with pure water 112. While the pressure test apparatus 111 is in an enclosed state, the contained pure water 112 is heated for generating water vapor, thereby increasing the inner pressure of the pressure test apparatus 111. The pressure test apparatus 111 has an unillustrated door. A user opens and closes the door for loading and unloading test samples (in the present embodiment, gas detection elements).

Figure 12:
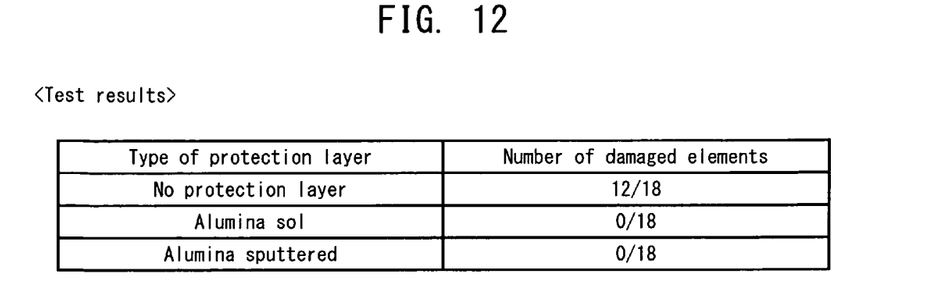
FIG. 12 is a table showing the results of Experiment 2.

FIG. 12 shows the number of damaged gas detection elements (gas detection elements whose heaters are damaged) for each type of the gas detection elements.

As shown in FIG. 12, among 18 bare elements 162, 12 bare elements 162 are damaged.

None of 18 alumina-sol protection layer elements 161 and 18 alumina-sputtered protection layer elements 160 are damaged.

The above experiment results show that a gas detection element whose outermost surface is a silicon nitride layer is weak in alkali resistance and is apt to be damaged by adhesion of an alkali substance.

By contrast, it has been confirmed from the above experiment results that a gas detection element whose outermost surface is an alkali resistant oxide film exhibits improved alkali resistance and is unlikely to be damaged even when an alkali substance adheres thereto.

As is apparent from the above experiment results, the gas detection element 60 of the gas detector 1 of the present embodiment has the protection layer 64 which has excellent alkali resistance and is impermeable to gas to thereby implement unlikeliness of adhesion of impurities (organic silicon), whereby the occurrence of damage stemming from adhesion of an alkali substance is restrained, and also adhesion of impurities (organic silicon) is restrained. By virtue of adhesion of impurities (organic silicon) being restrained, high detection accuracy can be attained.

That is, the gas detector 1 (more specifically, the gas detection element 60) of the present embodiment can implement high alkali resistance and high detection accuracy by means of formation of a gas impermeable oxide film (protection layer 64) on the outermost surface of the gas detection element 60.

In the present embodiment, the circuit board 41 corresponds to the control means of the present invention, and the protection layer 64 corresponds to the gas impermeable oxide film of the present invention.

While the present invention has been described with reference to the above embodiment, the present invention is not limited thereto, but may be embodied in various modes without departing from the technical scope of the present invention.

For example, in the above embodiment, the protection layer 64 can have a thickness of 20 nm to 500 nm. Also, the protection layer 64 can have a thickness equal to or greater than one-twentieth of that of the heat-generating resistor 71.

The above embodiment is described while mentioning the gas detection element 60 of the thermal-conductivity-type. However, the gas detection element 60 may be a catalytic-combustion-type gas detection element.

Also, the above embodiment is described while mentioning the detection of hydrogen gas. However, the gas detector 1 of the present invention can detect flammable gas of any other type.

| Description of Reference Numerals | |
|---|---|
| 1: | gas detector; |
| 10: | constant-temperature oven; |
| 11: | chamber; |
| 13: | gas inlet; |
| 14-17: | piping; |
| 18: | container; |
| 20: | element case; |
| 35: | inlet portion; |
| 39: | detection space; |
| 40: | housing case; |
| 41: | circuit board; |
| 42: | case body; |
| 50, 51: | heat-generating element; |
| 60: | gas detection element; |
| 61: | semiconductor substrate of silicon; |
| 64: | protection layer; |
| 71: | heat-generating resistor; |
| 80: | temperature-measuring resistor; |
| 85: | electrode; |
| 86: | ground electrode; |

-continued

| Description of Reference Numerals | |
|---|---|
| 88: | electrode; |
| 89: | ground electrode; |
| 90: | control circuit; |
| 94: | microcomputer; |
| 111: | pressure test apparatus; |
| 112: | pure water; and |
| 113: | table. |

Having described the invention, the following is claimed:

1. A gas detector comprising:
a gas detection element configured such that at least a heat-generating resistor and an insulation layer are laminated on a semiconductor substrate, and the insulation layer covers the heat-generating resistor; and
control means for controlling energization of the heat-generating resistor and detecting gas-to-be-detected on the basis of resistance of the energized heat-generating resistor;
wherein the gas detection element has an oxide film laminated on a surface of the insulation layer in such a manner as to cover the insulation layer, the oxide film impermeable to gas so as to restrain a change in thermal capacity of the gas detection element resulting from entry of organic silicon contained in a gaseous atmosphere into the gas detection element, and the gas impermeable oxide film forms an outermost surface layer which comes into contact with a gaseous atmosphere that contains the gas-to-be-detected.

2. A gas detector according to claim 1, wherein the surface of the insulation layer is of silicon nitride.

3. A gas detector according to claim 1, wherein the gas impermeable oxide film has a thickness equal to or greater than one-twentieth of a thickness of the heat-generating resistor as measured in a direction perpendicular to front and back surfaces of the semiconductor substrate.

4. A gas detector according to claim 1, wherein the gas impermeable oxide film has a thickness of 20 nm to 500 nm inclusive.

5. A gas detector according to claim 3, wherein the thickness of the gas impermeable oxide film is a distance between the surface of the insulation layer and a surface of the gas impermeable oxide film which comes into contact with the gaseous atmosphere.

6. A gas detector according to claim 1, wherein the gas impermeable oxide film is formed by a sputtering method.

7. A gas detector according to claim 1, wherein the gas detection element is a thermal-conductivity-type gas detection element or a catalytic-combustion-type gas detection element.

8. A gas detector according to claim 1, wherein the gas-to-be-detected is hydrogen gas.

9. A gas detector according to claim 1, wherein at least the gas detection element is disposed at a predetermined position on a fuel cell apparatus for generating electricity from hydrogen and oxygen, and is adapted to detect hydrogen gas used in the fuel cell apparatus.

10. A gas detector according to claim 4, wherein the thickness of the gas impermeable oxide film is a distance between the surface of the insulation layer and a surface of the gas impermeable oxide film which comes into contact with the gaseous atmosphere.

* * * * *